United States Patent [19]

Yates

[11] Patent Number: 4,940,825

[45] Date of Patent: Jul. 10, 1990

[54] PROCESS FOR REMOVING DICHLOROACETYLENE FROM 1,1-DICHLORO-1-FLUOROETHANE AND/OR VINYLIDENE CHLORIDE

[75] Inventor: Stephen F. Yates, Arlington Hts., Ill.

[73] Assignee: Allied-Signal Inc., Morris Township, Morris County, N.J.

[21] Appl. No.: 451,266

[22] Filed: Dec. 14, 1989

[51] Int. Cl.$^5$ ............................................. C07C 17/38
[52] U.S. Cl. ..................................................... 570/179
[58] Field of Search ......................................... 570/179

[56] References Cited

U.S. PATENT DOCUMENTS

| | | | |
|---|---|---|---|
| 2,894,044 | 7/1959 | Prill | 260/653.7 |
| 3,833,676 | 9/1974 | Ukaji et al. | 260/653.7 |
| 4,820,681 | 4/1989 | Chang et al. | 502/418 |
| 4,849,558 | 7/1989 | Goodman | 570/179 |

FOREIGN PATENT DOCUMENTS

| | | | |
|---|---|---|---|
| 1040436 | 2/1989 | Japan | 570/179 |
| 846677 | 8/1960 | United Kingdom | 570/179 |

OTHER PUBLICATIONS

Jüntgen et al., Fuel, 1981, vol. 60, Sep. pp. 817–822.
Chihara et al., Journal of Colloid and Interface Science, vol. 64, No. 3, May 1978, pp. 584–587.

*Primary Examiner*—Alan Siegel
*Attorney, Agent, or Firm*—Harold N. Wells; Jay P. Friedenson; Gerard P. Rooney

[57] ABSTRACT

Dichloroacetylene can be substantially removed from a stream of CFC-141b and/or vinylidene chloride over a carbon molecular sieve having a mean pore size of about 4.2 to 4.5 Angstroms.

6 Claims, 1 Drawing Sheet

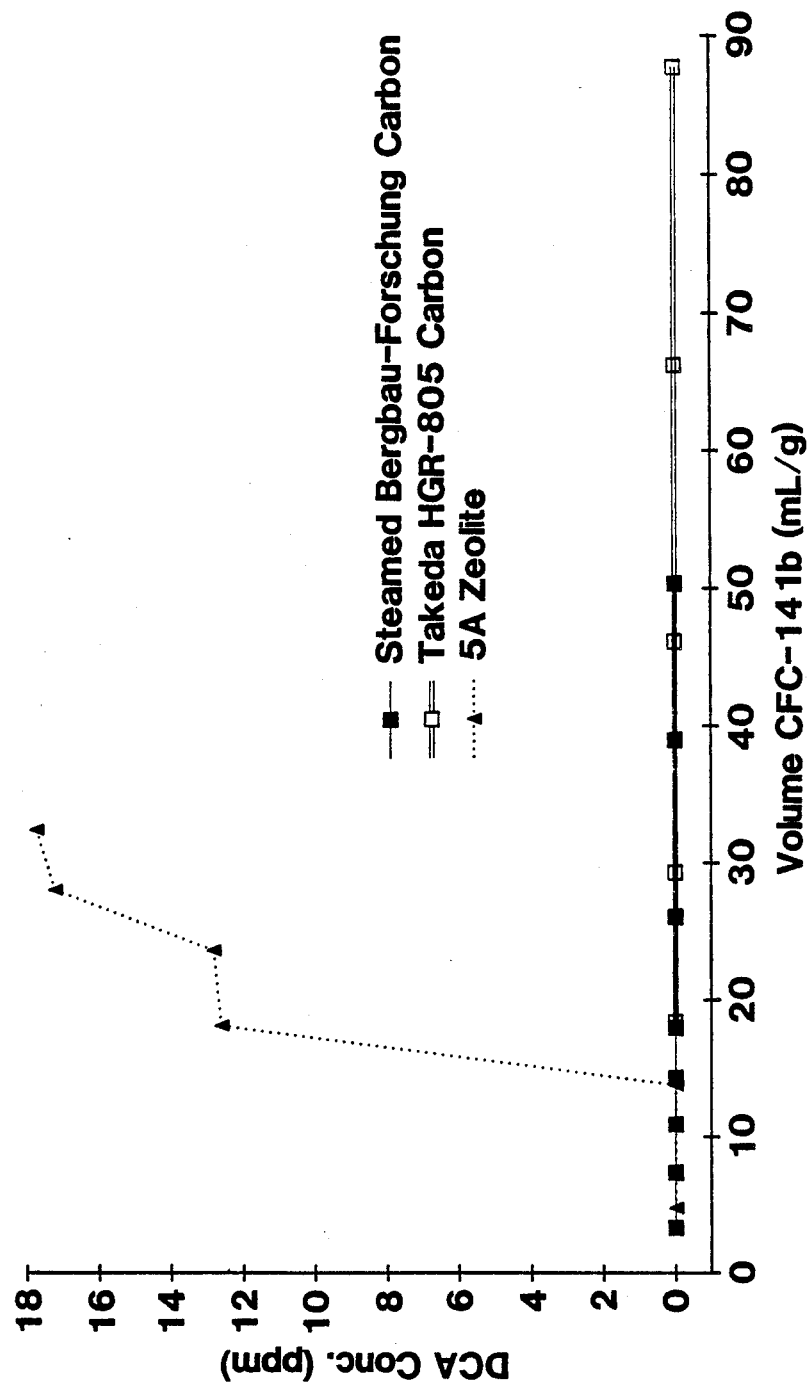

PROCESS FOR REMOVING DICHLOROACETYLENE FROM 1,1-DICHLORO-1-FLUOROETHANE AND/OR VINYLIDENE CHLORIDE

PRIOR ART

This invention relates to the purification of 1,1-dichloro-1-fluoroethane, also designated CFC-141b, which has been of particular interest as a replacement for chlorofluorocarbons having similar physical properties, particularly CFC-11, -12, and -113. CFC-141b may be prepared by reaction of vinylidene chloride or trichloroethane with HF. Such processes are disclosed, for example, in U.S. Pat. Nos. 2,894,044 and 3,833,676.

It is characteristic of such reactions that many by-products are formed, containing varying numbers of hydrogen, chlorine, and fluorine atoms on methane, ethane, and ethylene molecules. These by-products and the unreacted feed material may be separated by distillation where possible. Other compounds are relatively harmless since their presence does not greatly alter the physical properties for which CFC-141b is useful. A contaminant which must be removed because of its toxicity is dichloroacetylene, although only relatively small amounts are typically present in CFC-141b as formed and these are believed to have entered in the vinylidene chloride feed.

Further improvement in methods of purifying CFC-141b, particularly with respect to eliminating dichloroacetylene is desired and the present inventor has discovered a means for purification by adsorption which will be disclosed in detail below.

SUMMARY OF INVENTION

Dichloroacetylene can be substantially completely removed from a stream of CFC-141b initially containing about 4 to 20 ppm by weight of dichloroacetylene. The CFC-141b stream is passed over a carbon molecular sieve having a mean pore size between about 4.2 to 4.5 Angstroms at a temperature of about $-20°$ C. to $60°$ C. and a pressure of about 100 to 500 kPa. The removal of dichloroacetylene is essentially complete, that is, below the limit of detection of 2 wt. ppm. Alternatively, dichloroacetylene may be removed from vinylidene chloride before it is fed to the fluorination process.

The process may be carried out with CFC-141b (or vinylidene chloride) in the liquid or vapor phase. Where a fixed bed of zeolite particles is used, CFC-141b (or vinylidene chloride) vapor may be passed over the particles with a gas hourly space velocity of about 130 to 1500 hr$^{-1}$. The corresponding liquid space velocity for liquid phase operation would be about 1 to 15 hr$^{-1}$.

DESCRIPTION OF THE DRAWING

The sole FIGURE is a graph showing adsorption of dichloroacetylene on various carbon molecular sieves.

DESCRIPTION OF THE PREFERRED EMBODIMENTS

Adsorption of Dichloracetylene

Dichloroacetylene is present in CFC-141b in amounts between 4 and 20 ppm by weight and may be derived from the vinylidene chloride feed to the fluorination reaction.

It is preferred that a contaminant such as dichloroacetylene be removed selectively from CFC-141b. Distillation is commonly used but it is not useful for removing small amounts of dichloroacetylene. Adsorption may be considered for such applications. However, an adsorbent may remove more than the target compound, i.e. dichloroacetylene, and thus the cost of removing it increases and when the adsorbent is regenerated the target compound will be contaminated with other compounds. However, the present inventor has found that by selecting the proper molecular sieve nearly ideal separation of dichloroacetylene from CFC-141b can be achieved.

As will be seen in the examples below dichloroacetylene is not removed to any significant extent by many molecular sieve materials. However, carbon molecular sieves have been found to be useful which have a mean pore size of about 4.2 to 4.5 Angstroms.

Carbon Molecular Sieves

Carbon molecular sieves are available commercially. They are usually derived from natural sources such as coal. One example is the carbon molecular sieves described in a paper by Juntgen et al. of Bergbau-Forschung GmbH in *FUEL*, 1981, Vol. 60, September, p. 817-822.

Another carbon molecular sieve used for the purification of fluorocarbons is produced by a unique method disclosed in U.S. Pat. No. 4,820,681 and incorporated herein by reference. This method of manufacturing may be broadly characterized as comprising three steps: (1) polymerization of an oxygen-free monomer in the presence of an oxygen-free cross-linking agent; (2) forming particles of the resultant polymer into a desired shape; and then, (3) carbonizing the shaped material in a substantially oxygen-free environment.

The monomer can be chosen from a number of different monomers. They should be readily polymerizable, essentially free of oxygen in their molecular structure and preferably comprised basically of hydrogen, a halogen, and carbon. Among the materials which may be employed as the monomer are acrylonitrile (AN), vinylidene fluoride (PVDF), chlorotrifluoroethylene (HALAR), vinylidene chloride (PVDC), mixtures of two or more monomers such as mixtures of vinylidene chloride and vinyl chloride, vinylidene chloride and acrylonitrile, and a mixture of styrene and divinylbenzene. Other suitable monomers are vinyl fluoride, vinyl bromide, chlorinated ethylene, chlorofluorethylene, vinyl chlorobenzene, vinylidene bromide and vinylidenefluoridechlorotrifluoroethylene. The preferred monomer is vinylidene chloride. Polymerization reactions may be performed according to a number of different procedures known in the art. However, the most favorable results have been obtained employing a bulk polymerization or a solution polymerization.

The polymers produced in the initial polymerization step should be cross-linked with a substantially oxygen-free cross-linking agent. The cross-linking agent will typically be present during the polymerization at a concentration equal to less than 10 mole percent of the monomer. A preferred cross-linking agent is divinylbenzene. Other possible cross-linking agents include trivinyl benzene, divinyl acetylene, and divinyl sulfide.

As the production of carbon molecular sieves from polymers having a no-oxygen functionality is desired, the polymerization initiator is also preferably an oxygen-free compound. Therefore, a carbon or azo rather than an oxygen initiator is preferably used.

The polymeric material is carbonized by heating to a high temperature in an essentially oxygen-free environment. Prior to high temperature carbonization, the polymer precursor material is subjected to a mild heating step during which its temperature is raised above 150° C., e.g. 240° C., and held at this temperature until no more weight loss occurs. The material is then preferably subjected to a programmed temperature increase to a temperature above 700° C., preferably above 800° C., particularly, above 900° C. Sieve precursors derived from polymeric materials which are substantially free of the inorganic materials such as metals and inorganic oxides which may be present when the precursor material is made from a naturally occurring substance such as coal, coconut shells, peat, or wood. The preferred sieves, on a hydrogen- and oxygen-free basis, should contain at least 99.5 wt. % carbon and preferably at least 99.8 wt. % carbon.

While the just described method produces a unique and useful carbon molecular sieve, the average pore size is believed to be slightly above 3.8 Angstroms and accordingly, it must be further treated to increase the pore size to meet the needed size range. Various techniques may be used to increase the pore size, such as treatment with steam at temperatures between about 700° C. and 1000° C., treatment with air at temperatures between about 400° C. and 600° C., or treatment with $CO_2$ at temperatures between about 700° and 1000° C.

It should be noted that determination of the pore size of carbon molecular sieves is difficult and consequently, accurate values are not always available. Several approaches have been used. In the first method, a series of molecules of increasing size are brought in contact with the carbon molecular sieve and the amount adsorbed measured in a McBain balance. When amount of a molecule adsorbed is substantially greater than found with other molecules, the pore size is considered to have been determined. In the second method, a mixture of gases is tested for their behavior when a carbon molecular sieve is used as a chromatographic adsorbent. The pore size is estimated by observing which of these gases is retained on the adsorbent. Yet another method requires the measurement of the isosteric heat of adsorption of a gas or gases. The pore size is given by the intersection of a line drawn at this energy with the Lennard-Jones potential curve for that gas. An example of this last technique is given by K. Chihara et al. in the *Journal of Colloid and Interface Science*, 64, 584 (1978), in which the pore size of molecular sieve MSC-5A was found to be 4.4 Å.

Process

When CFC-141b is produced by catalytic hydrofluorination of a vinylidene chloride. Conversion to CFC-141b will be only partial and many by-products will be produced. Consequently, the reactor effluent will be separated by distillation to concentrate the CFC-141b product and to produce a recycle stream of unreacted feed. The resulting impure CFC-141b stream will contain unreacted HF and vinylidene chloride, and minor amounts of various by-product impurities, including dichloroacetylene which may be present in the vinylidene chloride feed. The HF and HCl can be removed selectively by a technique disclosed by others and not part of the present invention. Once done, the CFC-141b will still contain impurities which should be removed, particularly dichloroacetylene, which is toxic and must be removed. The present process is intended to be selective for removal of dichloroacetylene down to or below 2 ppm by weight from a concentrated CFC-141b stream.

The CFC-141b feed stream could be either in the liquid or gas phase, although the liquid phase would be preferred to avoid the costs of vaporizing and later condensing the feed stream. Various techniques known to those skilled in the art could be used for contacting the CFC-141b stream with the carbon molecular sieve adsorbent, such as fluidized or moving beds, but typically a packed bed of adsorbent particles would be used. Selection of the particle size, bed shape, and the space velocity of the CFC-141b stream would be determined according to known principles as required to provide nearly complete removal of dichloroacetylene. Generally, the gas hourly space velocity of the CFC-141b stream would be about 130 to 1500 $hr^{-1}$ when operating with a vapor feed. The corresponding liquid space velocity would be about 1 to 15 $hr^{-1}$. Adsorption would be carried out at a suitable temperature, generally between about −20° C. to 60 ° C. and a pressure dependent upon whether liquid or vapor contacting is desired, between about 100 to 500 kPa. As indicated in the examples below it may be expected that dichloroacetylene will be almost completely removed, leaving 2 ppm or less by weight in the CFC-141b stream ready for further purification if desired.

In an alternative embodiment dichloroacetylene is removed before fluorination of vinylidene chloride by passing the feed stream over the carbon molecular sieves in the same manner as discussed above with respect to CFC-141b.

The adsorbent bed should provide an optimum capacity for dichloroacetylene, balancing the costs for equipment and adsorbent versus the costs of regeneration. When the useful capacity has been reached, the adsorbent may be regenerated by heating the bed with a gas stream to remove the dichloroacetylene. Analysis of the off-gas suggests that dichloroacetylene is decomposed during heating since none has been detected. The CFC-141b remaining in the vessel and on the adsorbent will be removed first and recovered and then the regeneration process will be carried out. After the bed has been fully heated, it will be cooled and reintroduced to service. The conditions needed to optimally regenerate the adsorbent will be determined by the adsorbent used and the available utilities. Typically, it would be expected that heating the bed of adsorbent to about 200° C. to 500° C. with a stream of nitrogen would provide satisfactory regeneration.

EXAMPLE 1

A number of potential adsorbents were tested for their ability to remove vinylidene chloride. A sample of 15 mL of impure CFC-141b containing 576 wt. ppm vinylidene chloride, 16 wt. ppm of dichloroacetylene, 840 wt. ppm CFC-142b (1-chloro-1,1-difluoroethane), and 20 wt. ppm CFC-1131a (1-chloro-1-fluoroethylene) was placed in a 20 mL vial with 1.0 gm of the adsorbent to be tested. After agitating for 1 hour, a sample of the liquid was removed and analyzed by gas chromatography using two 3.175 mm diameter stainless columns in series (6.1 m of n-octane-Porasil C and 2 m of 10% OV-101 on Chromosorb W, both materials 80/100 mesh from Alltech Associates) and 18 mL/min of nitrogen as a carrier gas. The results are given in the Table below.

TABLE 1

| Absorbent | Dichloroacetylene wt. ppm |
| --- | --- |
| Feed (no adsorbent) | 16 |
| Chabazite (AW-500)[a] | <2 |
| 5A[b] | <2 |
| 3A[c] | 19 |
| Calcium X[d] | 19 |
| Mordenite (AW-300)[e] | 2.6 |
| Carbon Mol. Sieve[f] | 2.3 |
| Carbon Mol. Sieve[g] | <2 |
| Carbon Mol. Sieve[h] | <2 |
| Carbon Mole Sieve[i] | <2 |

[a] Supplied by UOP
[b] Supplied by UOP
[c] Supplied by UOP
[d] Supplied by UOP
[e] Supplied by UOP
[f] Prepared by procedure of U.S. 4,820,681 using polyvinylidene chloride carbonized at 800° C.
[g] Supplied by Takeda Chemical Co. (MSC-5A)
[h] Supplied by Bergbau-Forschung GmbH
[i] Supplied by Bergbau-Forschung GmbH and then steamed at 850° C. for 30 min.

Essentially none of the CFC-142b and CFC-1131a were removed.

It can be seen that most of the adsorbents did not adsorb dichloroacetylene. The 5A and chabazite were effective, but 5A has a low capacity (see Example 3), while chabazite appears to react with CFC-141b. The carbon molecular sieves were equally effective, but did not suffer these disadvantages. Note that carbon molecular sieve (f), which has a pore size somewhat larger than 3.8 Å, was less effective than sieves (g), (h) and (i), which have mean pore sizes between 4.2 and 4.5 Å.

EXAMPLE 2

Vinylidene chloride containing 8.2 ppm of dichloroacetylene was pumped at 0.88 mL/min through a 9.5 mm diameter column 177.8 mm long containing a carbon molecular sieve crushed to 20–50 mesh. The column was loaded with 6.125 g of a carbon molecular sieve supplied by Bergbau-Forschung which had been steamed at 850° C. Samples of the product were taken periodically and analyzed using the analytical method of Example 1. The results of this analysis are shown in the table below.

TABLE 2

| Sample | Volume Eluted (mL) | Dichloroacetylene Conc. |
| --- | --- | --- |
| 1 | 44 | none detected |
| 2 | 77 | none detected |
| 3 | 145 | 4.9 ppm |

EXAMPLE 3

CFC-141b containing 8.5 ppm of dichloroacetylene was pumped at 0.88 mL/min through a column of the same dimensions as in Example 2 containing 2–10 g of either 5A zeolite, carbon molecular sieve provided by Takeda Chemical Co. (HGR-805) or carbon molecular sieve provided by Bergbau-Forschung which had been subsequently treated with steam at 850° C. for 30 min. Samples of the product were taken periodically, and analyzed using the analytical method of Example 1. The results of this analysis are shown in the FIGURE. Note that dichloroacetylene broke through rapidly when 5A was the adsorbent, but that no dichloroacetylene was ever detected when either of the carbon molecular sieves were used.

I claim:

1. A process for purifying 1,1-dichloro-1-fluoroethane (CFC-141b) containing about 4–20 wt. ppm by weight of dichloroacetylene comprising passing said 1,1-dichloro-1-fluoroethane over a carbon molecular sieve having a mean pore size between about 4.2 to 4.5 Angstroms at a temperature of about −20° C. to 60° C. and a pressure of about 100 to 500 kPa and recovering 1,1-dichloro-1-fluoroethane containing less than 2 ppm by weight of dichloroacetylene.

2. The process of claim 1 wherein said carbon molecular sieve is a fixed bed of particles, the 1,1-dichloro-1-fluoroethane is a gas, and the gas hourly space velocity of said 1,1-dichloro-1-fluoroethane is about 130 to 1500 $hr^{-1}$.

3. The process of claim 1 wherein said carbon molecular sieve is a fixed bed of particles, the 1,1-dichloro-1-fluoroethane is a liquid, and the liquid hourly space velocity of said 1,1-dichloro-1-fluoroethane is about 1 to 15 $hr^{-1}$.

4. A process for purifying vinylidene chloride containing about 4 to 20 ppm by weight of dichloroacetylene comprising passing said vinylidene chloride over a carbon molecular sieve having a mean pore size between about 4.2 to 4.5 Angstroms at a temperature of −20 C. to 60° C. and a pressure of about 100 to 500 kPa and recovering vinylidene chloride containing less than 2 wt. ppm of dichloroacetylene.

5. The process of claim 4 wherein said carbon molecular sieve is a fixed bed of particles, the vinylidene chloride is a gas, and the gas hourly space velocity of said vinylidene chloride is about 130 to 1500 $hr^{-1}$.

6. The process of claim 4 wherein said carbon molecular sieve is a fixed bed of particles, the vinylidene chloride is a liquid, and the liquid hourly space velocity of said 1,1-dichloro-1-fluoroethane is about 1 to 15 $hr^{-1}$.

* * * * *